(12) United States Patent
Zlotnick et al.

(10) Patent No.: US 9,487,534 B2
(45) Date of Patent: Nov. 8, 2016

(54) MODULATORS OF VIRUS ASSEMBLY AS ANTIVIRAL AGENTS

(75) Inventors: Adam Zlotnick, Bloomington, IN (US); M. G. Finn, San Diego, CA (US)

(73) Assignees: Scripps Research Institute, A Not-for-Profit Public Benefit Corporation of California, La Jolla, CA (US); Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/236,428

(22) PCT Filed: Aug. 2, 2012

(86) PCT No.: PCT/US2012/049363
§ 371 (c)(1),
(2), (4) Date: Jan. 31, 2014

(87) PCT Pub. No.: WO2013/019967
PCT Pub. Date: Feb. 7, 2013

(65) Prior Publication Data
US 2015/0218182 A1    Aug. 6, 2015

Related U.S. Application Data

(60) Provisional application No. 61/514,179, filed on Aug. 2, 2011.

(51) Int. Cl.
| | |
|---|---|
| *C07D 403/12* | (2006.01) |
| *A61K 31/496* | (2006.01) |
| *C07D 491/113* | (2006.01) |
| *C07D 401/14* | (2006.01) |
| *C07D 401/04* | (2006.01) |
| *C07D 401/12* | (2006.01) |
| *C07D 239/20* | (2006.01) |
| *C07D 239/22* | (2006.01) |
| *C07D 417/04* | (2006.01) |
| *C07D 471/04* | (2006.01) |
| *C07D 491/10* | (2006.01) |
| *C07D 493/10* | (2006.01) |

(52) U.S. Cl.
CPC ......... *C07D 491/113* (2013.01); *A61K 31/496* (2013.01); *C07D 239/20* (2013.01); *C07D 239/22* (2013.01); *C07D 401/04* (2013.01); *C07D 401/12* (2013.01); *C07D 401/14* (2013.01); *C07D 403/12* (2013.01); *C07D 417/04* (2013.01); *C07D 471/04* (2013.01); *C07D 491/10* (2013.01); *C07D 493/10* (2013.01)

(58) Field of Classification Search
CPC  C07D 239/20; C07D 239/22; C07D 401/12; C07D 403/12; A61K 31/496

USPC ................. 540/524; 544/295, 333; 514/218, 514/252.14, 252.18, 256
See application file for complete search history.

(56) References Cited

U.S. PATENT DOCUMENTS

| | | | | |
|---|---|---|---|---|
| 4,728,652 | A * | 3/1988 | Atwal | 514/274 |
| 5,202,330 | A * | 4/1993 | Atwal et al. | 514/274 |
| 6,245,773 | B1 * | 6/2001 | Wong et al. | 514/272 |
| 6,436,943 | B1 | 8/2002 | Stoltefuss et al. | |
| 7,329,485 | B2 | 2/2008 | Zlotnick | |
| 2002/0107221 | A1 | 8/2002 | Schinazi et al. | |
| 2004/0058942 | A1 * | 3/2004 | Pullela et al. | 514/269 |
| 2010/0087448 | A1 | 4/2010 | Li et al. | |

FOREIGN PATENT DOCUMENTS

| | | | |
|---|---|---|---|
| WO | WO 01/68641 | * | 9/2001 |
| WO | WO 2010/069147 | * | 6/2010 |
| WO | WO 2010/148631 | * | 12/2010 |

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. I: Principles and Practice, pp. 975-977, 1995.*
Silverman, Prodrugs and Drug Delivery Systems, The Organic Chemistry of Drug Design and Drug Action, pp. 352-399, 1992.*
Zhang et al., Solid-Phase Synthesis of r-(2-(Benzylthio)-1,4-dihydro-6-methyl-4-p-tolylpyrimidine-5-carboxamido) Acids: a New Strategy toCreate Diversity in Heterocyclic Scaffolds, J. Comb. Chem., vol. 6, No. 4, pp. 457-459 and Supporting Information 2: Spectra (43 pages)(2004).*
Rana et al., Synthesis and anti-hypertensive activity of some dihydropyrimidines, Indian Journal of Chemistry, Section B, vol. 43B, pp. 1553-1557 (Jul. 2004).*
Kumar et al., Thermal/microwave assisted synthesis of substituted tetrahydropyrimidines as potent calcium channel blockers, Indian Journal of Chemistry, 41B(7), pp. 1526-1530 (2002).*
Singh et al., Synthesis of 2-sulfanyl-6-methyl-1,4-dihydropyrimidines as a new class of antifilarial agents, European Journal of Medicinal Chemistry, 43, pp. 2717-2723 (2008).*

(Continued)

*Primary Examiner* — Deepak Rao
(74) *Attorney, Agent, or Firm* — Faegre Baker Daniels LLP

(57) ABSTRACT

In addition to containing and protecting the viral genome, the capsid (protein shell) of hepatitis B virus (HBV) plays critical roles in the viral life cycle including regulation of intracellular trafficking and nucleic acid metabolism. Substituted pyrimidine modulators of the assembly of the HBV capsid structure and methods for their use are described.

12 Claims, 3 Drawing Sheets

(56) References Cited

OTHER PUBLICATIONS

Klein et al., New chemical tools for investigating human mitotic kinesin Eg5, Bioorganic & Medicinal Chemistry, 15, pp. 6474-6488 (2007).*

Maddila et al., Synthesis and Biological Activity of Ethyl 2-(substituted benzylthio)-4-(3 0-(ethoxycarbonyl)biphenyl-4-yl)-6-methyl-1,4-dihydropyrimidine-5-carboxylate Derivatives, Arch. Pharm. Chem. Life Sci., vol. 345, Issue 2, pp. 163-168 (Oct. 2011).*

Rana et al., Synthesis and Anti-ulcer Activity of Some Dihydropyrimidines, International Journal of Pharmaceutical Sciences and Drug Research, vol. 3, Issue 3, pp. 226-229 (Jul.-Sep. 2011).*

WO 2010/069147—Machine translation of claims, 2010.*

PCT International Search Report and Written Opinion established in connection with PCT/US2012/049363 and completed on Nov. 27, 2012.

Bourne, et al. "Small-Molecule Effectors of Hepatitis B Virus Capsid Assembly Give Insight into Virus Life Cycle" J. Virology, 2008, vol. 82, p. 10262-10270; Table 1, pp. 10264-10265, structures.

* cited by examiner

MODULATORS OF VIRUS ASSEMBLY AS ANTIVIRAL AGENTS

This application is a U.S. national counterpart application of international application serial No. PCT/US2012/049363 filed Aug. 2, 2012, which claims priority under 35 USC §119(e) to U.S. Provisional Patent Application No. 61/514,179, filed on Aug. 2, 2011, the entire disclosures of which are hereby incorporated by reference.

STATEMENT REGARDING FEDERALLY SPONSORED RESEARCH OR DEVELOPMENT

This invention was made with government support under AI067417 awarded by the National Institutes of Health. The Government has certain rights in the invention.

TECHNICAL FIELD

This application pertains to substituted dihydropyrimidines and their use as antivirals.

BACKGROUND AND SUMMARY OF THE INVENTION

The hepatitis B virus (HBV), which belongs to the hepadnavirus family, is a causative agent of acute and chronic hepatitis. HBV infections are the world's ninth leading cause of death. HBV infection often leads to acute hepatitis and liver damage, and causes abdominal pain, jaundice, and elevated blood levels of certain enzymes. HBV can cause fulminant hepatitis, a rapidly progressive form of the disease in which massive sections of the liver are destroyed. Many patients recover from acute viral hepatitis, but in certain other patients, especially young children, viral infection persists for an extended, or indefinite, period, causing a chronic infection. Chronic infections can lead to chronic persistent hepatitis. Chronic persistent hepatitis can cause fatigue, liver damage, cirrhosis of the liver, and hepatocellular carcinoma, a primary liver cancer.

HBV infection is a serious problem among the homo- and heterosexual population, intravenous drug users, organ transplant recipients, and blood transfusion patients. New infection with HBV can be prevented by vaccination. However, the present vaccination is not effective for the approximately 350 million chronic carriers worldwide. It has been observed that suppression or eradication of the replication of HBV in the liver leads to improved liver pathology and decreased progression to liver cirrhosis and hepatocellular carcinoma.

One of the current therapies approved in the United States for treating chronic hepatitis B infection is alpha interferon, which is far from ideal. According to the American Liver Foundation and the International Hepatitis Foundation, patients with conditions such as advanced hepatitis, HIV co-infection, drug abuse or others are not eligible for this treatment, resulting in less than 50% of chronic carriers obtaining this therapy. Of these patients, only about 40% respond to the treatment. Many of these patients also relapse after treatment is stopped, and only about 30% of the patients show a long term benefit. Viral disappearance is only seen in about 10-20% of the treated patients. These data suggest that there is an extremely low response rate in patients treated with alpha interferon. In addition to the low response rate, interferon therapy causes severe side effects such as insomnia, depression, nausea, vomiting, fever and fatigue. Another approved class of drugs for treating HBV infection is reverse transcriptase inhibitors exemplified by lamivudine, entecavir, and tenofovir. Although reverse transcriptase inhibitors have good antiviral activity, resistance can develop rapidly during treatment, there is cross-reactivity of resistance, and side effects such as kidney damage. There is also cross-reactivity between reverse transcriptase inhibitors for HBV and HIV. Furthermore, reverse transcriptase inhibitors are not known to lead to HBV clearance and, worse, discontinuation of the therapy is known to lead to a rebound effect occurs in most cases that can be life threatening.

Targeting assembly of the HBV capsid protein (CP), which has no human homolog, may be a powerful, general approach for developing anti-HBV therapeutics. It has been found that heteroaryldihydropyrimidines (HAPs) can enhance the rate and extent of CP assembly over a broad concentration range leading to aberrant particles, dominated by hexagonal arrays of CP. HAPs can also stabilize virus cores, preventing normal dissociation and release of the genome. Without being bound by theory, it is believed that the compounds described herein can disrupt HBV assembly, altering either the timing of formation of the capsid, the stability of the capsid, or the geometry of capsid formation, and interfering with viral infection. It is appreciated that enhancing the rate of CP aggregation and/or the rate for capsid assembly can deplete the concentration of CP, resulting in inhibition of non-structural activities mediated by CP.

In one illustrative embodiment of the invention, a compound having the formula

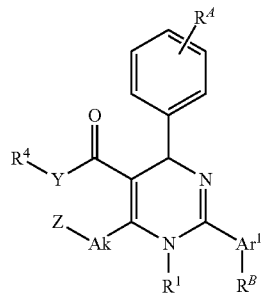

or a pharmaceutically acceptable salt thereof is described, wherein $Ar^1$ is selected from the group consisting of phenyl, 2-pyridyl, 3-pyridyl, and 4-pyridyl;

$R^1$ is hydrogen or pro-drug forming group;

Ak is alkylene;

Z is

where X is $CHN_3$, $C=O$, $C=NR^5$, $-C(O)N(R^N)-$, or $NR^N$, where $R^5$ is hydroxy or a derivative thereof or amino or a derivative thereof, and $R^N$ is selected from the group consisting of alkyl, alkenyl, alkynyl, heteroalkyl, arylalkyl, heteroarylalkyl, alkyl-C(O), heteroalkyl-C(O), alkoxyl-C(O), alkynyl-C(O), alkylacylamino-C(O), and heteroalkylacylamino-C(O), each of which is optionally substituted;

$R^4$ is alkyl, heteroalkyl, alkenyl, or alkynyl, each of which is optionally substituted;

Y is O, or HN;

$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and $R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

In another illustrative embodiment, a compound having the formula

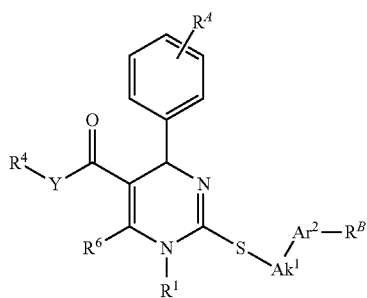

or a pharmaceutically acceptable salt thereof is described, wherein;

$Ar^2$ is aryl or heteroaryl each of which is optionally substituted;

$R^1$ is independently in each instance selected from the group consisting of hydrogen and pro-drug forming group;

$R^4$ is alkyl, heteroalkyl, alkenyl, or alkynyl, each of which is optionally substituted;

Y is O, or HN;

$R^6$ is in each instance independently selected from the group consisting of hydrogen and Ak-$Z^1$, where Ak is alkylene, and $Z^1$ is independently in each instance hydrogen or $NR^2R^3$; where $R^2$ and $R^3$ are independently in each instance hydrogen, or selected from the group consisting of alkyl, cycloalkyl, heteroalkyl and heterocycloalkyl, each of which is optionally substituted, or $R^2$ and $R^3$ are taken together with the attached nitrogen to form

wherein X is $CHN_3$, C=O, —C(O)N($R^{Na}$)—, C=$NR^5$, or $NR^{Na}$; where $R^5$ is hydroxy or a derivative thereof or amino or a derivative thereof; and $R^{Na}$ is selected from the group consisting of hydrogen, and alkyl, alkenyl, alkynyl, heteroalkyl, arylalkyl, heteroarylalkyl, alkyl-C(O), heteroalkyl-C(O), alkoxyl-C(O), alkynyl-C(O), alkylacylamino-C(O), and heteroalkylacylamino-C(O), each of which is optionally substituted;

$Ak^1$ is $(CH_2)n$, where n is 1 to 4;

$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and $R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

In addition, various genera and subgenera of each of $R^1$, $R^2$, $R^3$, $R^4$, $R^5$, $R^6$, $Ar^1$, $Ar^2$, X, Ak, $Ak^1$, $R^A$, $R^B$, and Z are described herein. It is to be understood that all possible combinations of the various genera and subgenera of each of $R^1$, $R^2$, $R^3$, $R^4$, $R^5$, $R^6$, $Ar^1$, $Ar^2$, X, Ak, $Ak^1$, $R^A$, $R^B$, and Z described herein represent additional illustrative embodiments of compounds of the invention described herein. It is to be further understood that each of those additional illustrative embodiments of compounds may be used in any of the compositions, methods, and/or uses described herein.

In another embodiment, pharmaceutical compositions containing one or more of the compounds are also described herein. In one aspect, the compositions include a therapeutically effective amount of the one or more compounds for treating a patient with hepatitis B. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with hepatitis B are also described herein. In one aspect, the methods include the step of administering one or more of the compounds and/or compositions described herein to a patient with hepatitis B. In another aspect, the methods include administering a therapeutically effective amount of the one or more compounds and/or compositions described herein for treating patients with hepatitis B. In another embodiment, uses of the compounds and compositions in the manufacture of a medicament for treating patients with hepatitis B are also described herein. In one aspect, the medicaments include a therapeutically effective amount of the one or more compounds and/or compositions for treating a patient with hepatitis B.

It is appreciated herein that the compounds described herein may be used alone or in combination with other compounds useful for treating hepatitis B, including those compounds that may be therapeutically effective by the same or different modes of action. In addition, it is appreciated herein that the compounds described herein may be used in combination with other compounds that are administered to treat other symptoms of hepatitis B.

DETAILED DESCRIPTION

Figure 1:
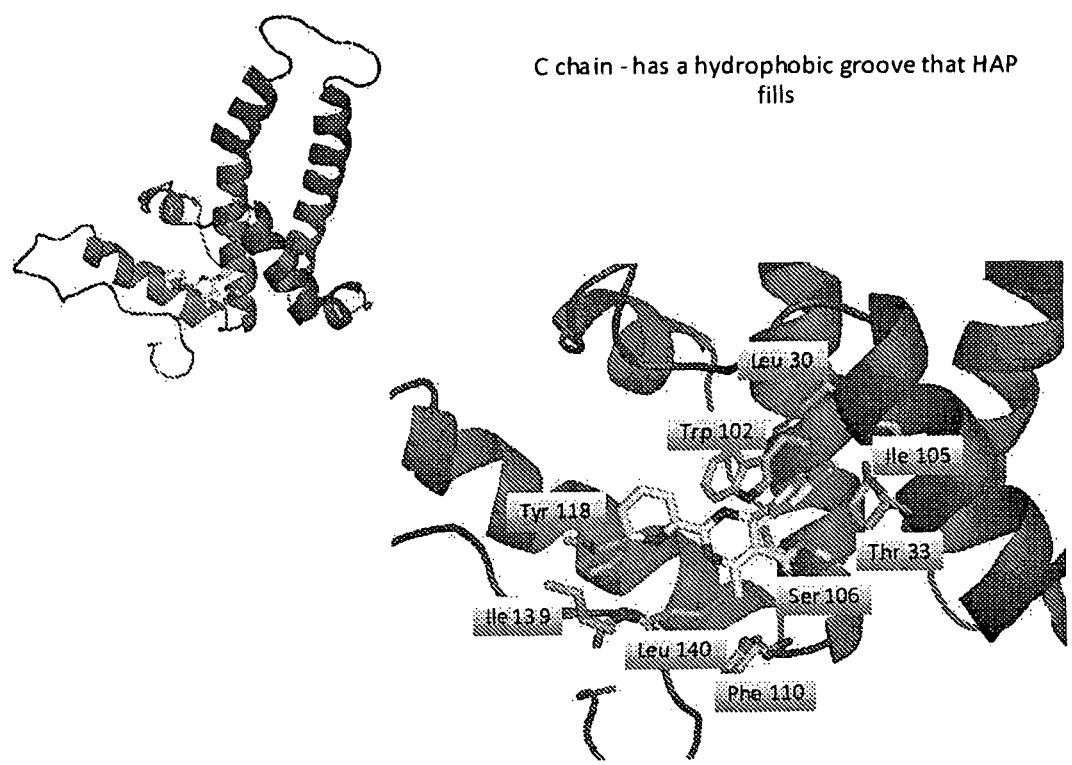
FIG. 1 shows the binding of a heteroaryldihydropyrimidine in a hydrophobic groove in the C chain of a capsid protein of hepatitis B virus (HBV).
Figure 2:
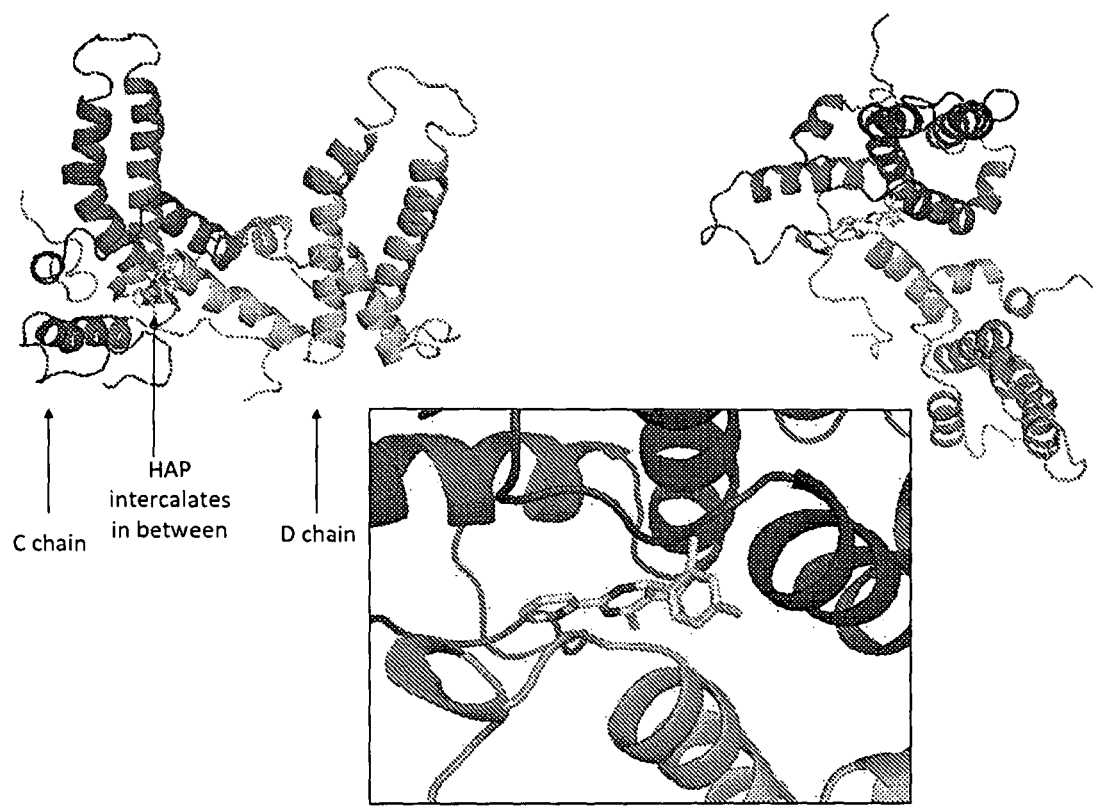
FIG. 2 shows a heteroaryldihydropyrimidine intercalating between a C chain and D chain of the HBV capsid proteins
Figure 3:
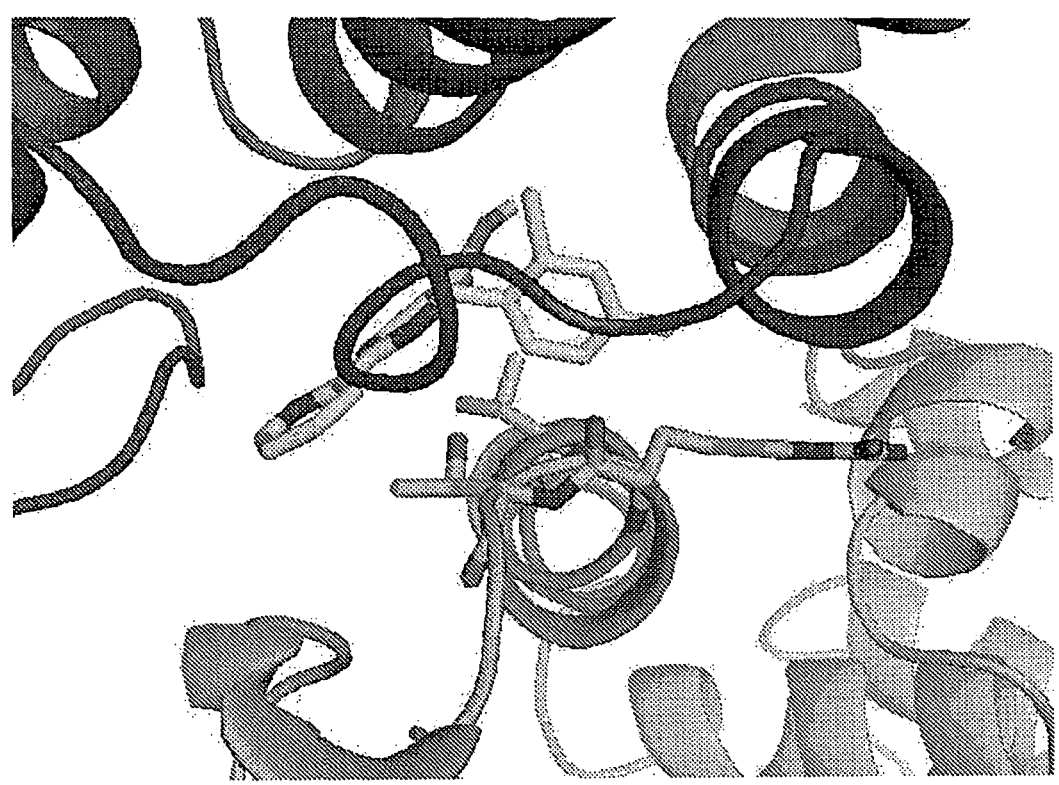
FIG. 3 shows another view of the heteroaryldihydropyrimidine intercalating between a C chain and D chain of the HBV capsid proteins as shown in FIG. 2.

Several illustrative embodiments of the invention are described by the following enumerated clauses:
1. A compound having the formula

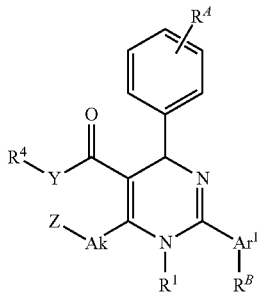

or a pharmaceutically acceptable salt thereof, wherein
Ar¹ is selected from the group consisting of phenyl, 2-pyridyl, 3-pyridyl, and 4-pyridyl;
R¹ is hydrogen or pro-drug forming group;
Ak is alkylene;
Z is

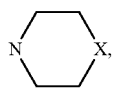

where X is $CHN_3$, $C=O$, $C=NR^5$, $C(O)NR^N$, or $NR^N$, where $R^5$ is hydroxy or a derivative thereof or amino and derivatives thereof, and $R^N$ is selected from the group consisting of alkyl, alkenyl, alkynyl, heteroalkyl, alkylaryl, alkylheteroaryl, C(O)alkyl, C(O)heteroalkyl, C(O)alkoxyl, C(O)alkynyl, C(O)alkylacylamino, and C(O)heteroalkylacylamino, each of which is optionally substituted;
$R^4$ is alkyl, heteroalkyl, alkenyl, or alkynyl, each of which is optionally substituted;
Y is O, or HN;
$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted;
$R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted; and where the compound is not

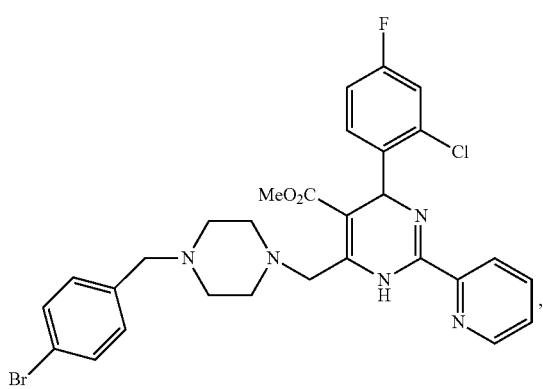

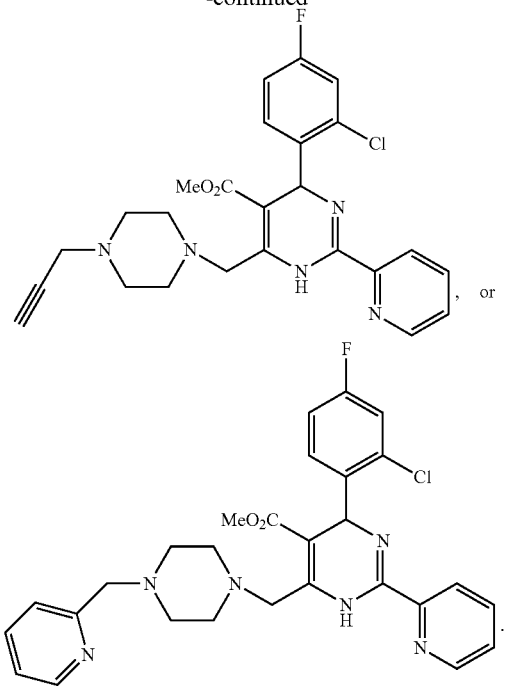

, or

2. A compound having the formula

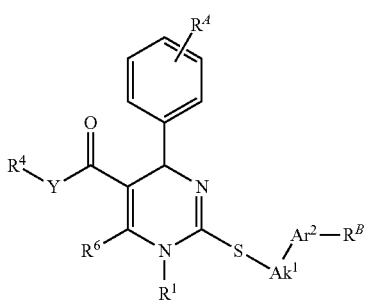

or a pharmaceutically acceptable salt thereof, wherein;
Ar² is aryl or heteroaryl each of which is optionally substituted;
R¹ is independently in each instance selected from the group consisting of hydrogen and pro-drug forming group;
$R^4$ is alkyl, heteroalkyl, alkenyl, or alkynyl, each of which is optionally substituted;
Y is O, or HN;
$R^6$ is in each instance independently selected from the group consisting of hydrogen and Ak-Z¹, where Ak is alkyl, and Z¹ is independently in each instance hydrogen or $NR^2R^3$; where R² and R³ are independently in each instance hydrogen, or selected from the group consisting of alkyl, cycloalkyl, heteroalkyl and heterocycloalkyl, each of which is optionally substituted, or
R² and R³ are taken together with the attached nitrogen to form

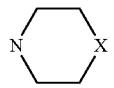

X is $CHN_3$, C=O, $C(O)NR^N$, $C=NR^5$, where $R^5$ is hydroxy or a derivatives thereof or amino or a derivative thereof; or $NR^{Na}$, where $R^{Na}$ is hydrogen or selected from the group consisting of alkyl, alkenyl, alkynyl, heteroalkyl, alkylaryl, alkylheteroaryl, C(O)alkyl, C(O)heteroalkyl, C(O)alkoxyl, C(O)alkynyl, C(O)alkylacylamino, and C(O)heteroalkylacylamino, each of which is optionally substituted;

$Ak^1$ is $(CH_2)n$, where n is 1 to 4;

$R^A$ represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and $R^B$ represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

3. The compound of clause 1 or 2 to wherein $R^A$ represents 2-c-4-fluoro.

4. The compound of clause 1 wherein $Ar^1$ is 2-pyridyl.

5. The compound of any one of clauses 1 to 4 wherein $R^B$ is absent.

6. The compound of any one of clauses 1 to 5 wherein Y is O.

7. The compound of any one of clauses 1 to 6 wherein $R^4$ is methyl.

8. The compound of clause 2 wherein $R^6$ is methyl.

9. The compound of clause 2 wherein $R^6$ is

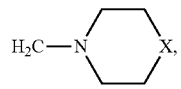

where X is $CHN_3$, C=O, $C(O)NR^N$, $C=NR^5$, where $R^5$ is hydroxy or a derivative thereof or amino or a derivative thereof; or $NR^N$, where $R^N$ is independently in each instance hydrogen or selected from the group consisting of alkyl, alkenyl, alkynyl, heteroalkyl, alkylaryl, alkylheteroaryl, C(O)alkyl, or C(O)heteroalkyl, C(O)alkylacylamino, and C(O)heteroalkylacylamino, each of which is optionally substituted.

10. The compound of clause 1 where in Ak is methylene; and Z is

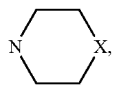

where X is $CHN_3$, C=O, $C(O)NR^N$, $C=NR^5$, where $R^5$ is hydroxy and derivatives thereof or amino and derivatives thereof; or $NR^N$, where $R^N$ is independently in each instance hydrogen or selected from the group consisting of alkyl, alkenyl, alkynyl, heteroalkyl, alkylaryl, alkylheteroaryl, C(O)alkyl, or C(O)heteroalkyl, C(O)alkylacylamino, and C(O)heteroalkylacylamino, each of which is optionally substituted.

11. The compound of clause 10 wherein X is C=O, $C(O)NR^N$, or $NR^N$, where $R^N$ is independently in each instance hydrogen or selected from the group consisting of alkyl, alkenyl, alkynyl, heteroalkyl, alkylaryl, alkylheteroaryl, C(O)alkyl, C(O)heteroalkyl, C(O)alkylacylamino, and C(O)heteroalkylacylamino, each of which is optionally substituted.

11.1 The compound of clause 9 wherein X is C=O, $C(O)NR^{Na}$, or $NR^{Na}$, where $R^{Na}$ is independently in each instance hydrogen or selected from the group consisting of alkyl, alkenyl, alkynyl, heteroalkyl, alkylaryl, alkylheteroaryl, C(O)alkyl, C(O)heteroalkyl, C(O)alkylacylamino, and C(O)heteroalkylacylamino, each of which is optionally substituted.

11.2 The compound of clause 11 or 11.1 wherein X is N=OH.

11.3 The compound of clause 11 or 11.1 wherein X is C(O)NH.

12. The compound of clause 11 or 11.1 wherein X is C=O.

13. A pharmaceutical composition comprising a therapeutically effective amount of one or more compounds of any one of clauses 1 to 12 for treating hepatitis B.

14. The composition of clause 13 further comprising one or more carriers, diluents, or excipients, or a combination thereof.

15. A method for treating hepatitis B, the method comprising the step of administering to a patient in need of relief from hepatitis B the composition of clauses 13 or 14 or a therapeutically effective amount of one or more compounds of any one of clauses 1 to 12.

15. A method for treating a patient in need of relief from infection by hepatitis B virus, the method comprising the step of administering to the patient the composition of claim 13 or 14 or a therapeutically effective amount of one or more compounds of any one of claims 1 to 12.

16. The method of clause 15 wherein the treating includes ameliorating symptoms or inhibiting chronic infection by hepatitis B virus.

17. The method of clause 15 wherein the infection is a chronic infections

18. The method of clause 15 wherein the infection is an acute infection.

19. The method of clause 17 or 18 wherein the compound acts by activating assembly of the virus core disrupting the normal timing of virus production in an infected cell.

18. The method of clause 17 or 18 wherein the compound acts by activating assembly of the virus core disrupting the normal timing of virus production in an infected cell.

19. The method of clause 17 or 18 wherein the compound acts by stabilizing existing capsids inhibiting dissociation of the virus core and release of its genome in the nucleus.

20. A compound having the formula

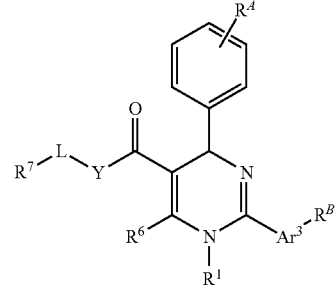

or a pharmaceutically acceptable salt thereof is described, wherein;

Ar³ is aryl or heteroaryl each of which is optionally substituted;

R¹ is independently in each instance selected from the group consisting of hydrogen and pro-drug forming group;

R⁴ is alkyl, heteroalkyl, alkenyl, or alkynyl, each of which is optionally substituted;

Y is O, or HN;

R⁶ is in each instance independently selected from the group consisting of hydrogen and Ak-Z¹, where Ak is alkylene, and Z¹ is independently in each instance hydrogen or NR²R³; where R² and R³ are independently in each instance hydrogen, or selected from the group consisting of alkyl, cycloalkyl, heteroalkyl and heterocycloalkyl, each of which is optionally substituted, or R² and R³ are taken together with the attached nitrogen to form

X is CHN₃, C=O, C(O)NR^N, C=NR⁵, where R⁵ is hydroxy and derivatives thereof or amino and derivatives thereof; or NR^N, where R^N is independently in each instance hydrogen or selected from the group consisting of alkyl, alkenyl, alkynyl, heteroalkyl, alkylaryl, alkylheteroaryl, C(O)alkyl, or C(O)heteroalkyl, C(O)alkylacylamino, or C(O)heteroalkylacylamino, each of which is optionally substituted;

L is

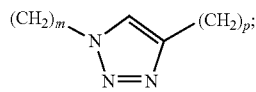

R⁷ is Ar⁴L² or

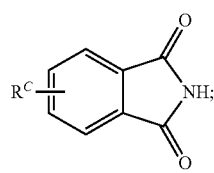

where Ar⁴ is optionally substituted aryl or heteroaryl, and L² is C(O)O, C(O)NH, or S(O)₂NH Ak¹ is (CH₂)n, where n is 1 to 4;

R^A represents from 0 to 3 substituents independently in each instance, halo or selected from the group consisting of alkyl, heteroalkyl, aryl, heteroaryl, amino and derivatives thereof, and hydroxyl and derivatives thereof, each of which is optionally substituted; and R^B represents from 0 to 3 substituents independently in each instance, halogen or selected from the group consisting of alkyl, heteroalkyl, aryl, heteroaryl, amino and derivatives thereof, and hydroxyl and derivatives thereof, each of which is optionally substituted.

21. A pharmaceutical composition comprising a therapeutically effective amount of one or more compounds of clause 20 for treating hepatitis B.

22. A method for treating a patient in need of relief from infection by hepatitis B virus, the method comprising the step of administering to the patient the composition of clause 21 or a therapeutically effective amount of one or more compounds of clause 21.

23. A composition comprising one or more compounds of any one of clauses 1 to 12 or 20 for treating hepatitis B.

Several additional illustrative embodiments of the invention are described by the following enumerated clauses:

101. A compound of the formula

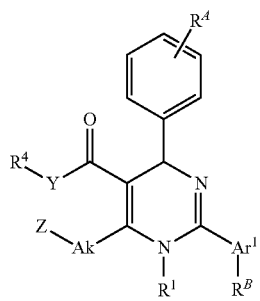

or a pharmaceutically acceptable salt thereof, wherein

Ar¹ is selected from the group consisting of phenyl, 2-pyridyl, 3-pyridyl, and 4-pyridyl;

R¹ is hydrogen or pro-drug forming group;

Ak is alkylene;

Z is

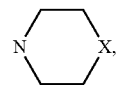

where X is CHN₃, C=O, C=NR⁵, —C(O)N(R^N)—, or NR^N, where R⁵ is hydroxy or a derivative thereof or amino or a derivative thereof, and R^N is selected from the group consisting of alkyl, alkenyl, alkynyl, heteroalkyl, arylalkyl, heteroarylalkyl, alkyl-C(O), heteroalkyl-C(O), alkoxyl-C(O), alkynyl-C(O), alkylacylamino-C(O), and heteroalkylacylamino-C(O), each of which is optionally substituted;

R⁴ is alkyl, heteroalkyl, alkenyl, or alkynyl, each of which is optionally substituted;

Y is O, or HN;

R^A represents from 0 to 3 substituents independently selected in each instance from the group consisting of halo, and alkyl, heteroalkyl, aryl, heteroaryl, amino and derivatives thereof, and hydroxyl and derivatives thereof, each of which is optionally substituted;

R^B represents from 0 to 3 substituents independently selected in each instance from the group consisting of halo, and alkyl, heteroalkyl, aryl, heteroaryl, amino and derivatives thereof, and hydroxyl and derivatives thereof, each of which is optionally substituted; and where the compound is not

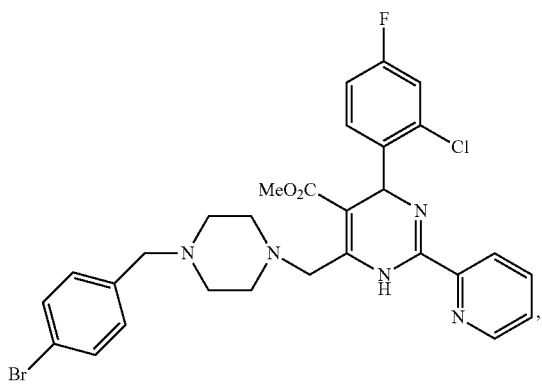

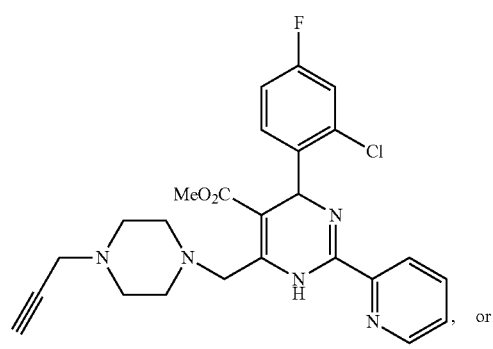

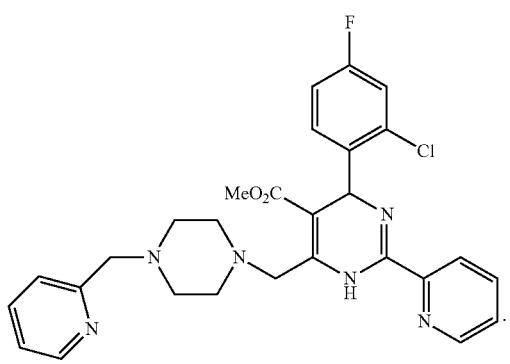

102. The compound of clause 101 wherein $R^A$ represents 2-cholor-4-fluoro.

103. The compound of any one of the preceding clauses wherein $Ar^1$ is 2-pyridyl.

104. The compound of any one of the preceding clauses wherein $R^B$ represents 0 substituents.

105. The compound of any one of the preceding clauses wherein Y is O.

106. The compound of any one of the preceding clauses wherein $R^4$ is methyl.

107. The compound of any one of the preceding clauses where in Ak is methylene.

108. The compound of any one of the preceding clauses wherein X is C=O, —C(O)N($R^N$)—, or $NR^N$.

109. The compound of any one of the preceding clauses wherein X is C=O.

110. A compound of the formula

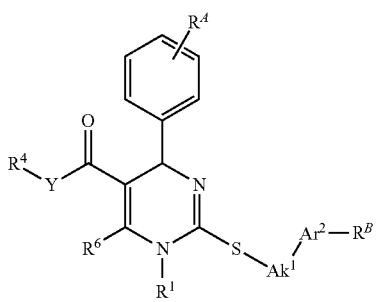

or a pharmaceutically acceptable salt thereof, wherein;
$Ar^2$ is aryl or heteroaryl;
$R^1$ is hydrogen or a pro-drug forming group;
$R^4$ is alkyl, heteroalkyl, alkenyl, or alkynyl, each of which is optionally substituted;
Y is O, or HN;
$R^6$ is in each instance independently selected from the group consisting of hydrogen and Ak-$Z^1$, where Ak is alkylene, and $Z^1$ is hydrogen or $NR^2R^3$; where $R^2$ and $R^3$ are independently in each instance selected from the group consisting of hydrogen, and alkyl, cycloalkyl, heteroalkyl and heterocycloalkyl, each of which is optionally substituted, or
$R^2$ and $R^3$ are taken together with the attached nitrogen to form

wherein X is $CHN_3$, C=O, —C(O)N($R^{Na}$)—, C=$NR^5$, or $NR^{Na}$; where $R^5$ is hydroxy or a derivative thereof or amino or a derivative thereof; and $R^{Na}$ is selected from the group consisting of hydrogen, and alkyl, alkenyl, alkynyl, heteroalkyl, arylalkyl, heteroarylalkyl, alkyl-C(O), heteroalkyl-C(O), alkoxyl-C(O), alkynyl-C(O), alkylacylamino-C(O), and heteroalkylacylamino-C(O), each of which is optionally substituted;
$Ak^1$ is $(CH_2)n$, where n is 1 to 4;
$R^A$ represents from 0 to 3 substituents independently selected in each instance from the group consisting of halo, and alkyl, heteroalkyl, aryl, heteroaryl, amino and derivatives thereof, and hydroxyl and derivatives thereof, each of which is optionally substituted; and
$R^B$ represents from 0 to 3 substituents independently selected in each instance from the group consisting of halo, and alkyl, heteroalkyl, aryl, heteroaryl, amino and derivatives thereof, and hydroxyl and derivatives thereof, each of which is optionally substituted.

111. The compound of clause 110 wherein $R^6$ is methyl.

112. The compound of clause 110 or 111 wherein $R^6$ is

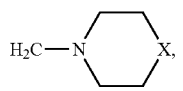

where X is $CHN_3$, C=O, —C(O)N($R^{Na}$)—, C=$NR^5$, or $NR^{Na}$; where $R^5$ is hydroxy or a derivative thereof or amino or a derivative thereof; and $R^{Na}$ is hydrogen or alkyl, alkenyl, alkynyl, heteroalkyl, arylalkyl, heteroarylalkyl, alkyl-C(O), heteroalkyl-C(O), alkoxyl-C(O), alkynyl-C(O), alkylacylamino-C(O), or heteroalkylacylamino-C(O), each of which is optionally substituted.

113. The compound of any one of clauses 110 to 112 wherein X is C=O, —C(O)N(R$^{Na}$)—, or NR$^{Na}$, where R$^{Na}$ is hydrogen or alkyl, alkenyl, alkynyl, heteroalkyl, arylalkyl, heteroarylalkyl, alkyl-C(O), heteroalkyl-C(O), alkylacylamino-C(O), and heteroalkylacylamino-C(O), each of which is optionally substituted.

114. The compound of any one of clauses 110 to 113 wherein X is C=O.

115. A pharmaceutical composition comprising a therapeutically effective amount of one or more compounds of any one of the preceding clauses for treating hepatitis B.

116. The composition of clause 115 further comprising one or more carriers, diluents, or excipients, or a combination thereof.

117. A method for treating a patient in need of relief from infection by hepatitis B virus, the method comprising the step of administering to the patient a therapeutically effective amount of one or more compounds of any one of the preceding compound or composition clauses.

118. The method of clause 117 wherein the treating includes ameliorating symptoms or inhibiting chronic infection by hepatitis B virus.

119. The method of clause 117 or 118 wherein the infection is a chronic infection.

120. The method of clause 117 or 118 wherein the infection is an acute infection.

121. The method of any one of the preceding method clauses wherein the compound acts by activating assembly of the virus core disrupting the normal timing of virus production in an infected cell.

122. The method of any one of the preceding method clauses wherein the compound acts by stabilizing existing capsids in an infected cell inhibiting dissociation of the virus core and release of the viral genome in the cell nucleus.

123. The method of any one of the preceding method clauses wherein the compound affects the viral lifecycle by inducing assembly of the viral core lowering the concentration of unassembled hepatitis B virus capsin protein and inhibiting a non-structural activity of the capsid protein.

124. The method of any one of the preceding method clauses wherein the compound acts on the viral lifecycle by binding to free capsid protein dimer inhibiting a capsid protein non-structural activity.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

In another embodiment, the following illustrative compounds are a described.

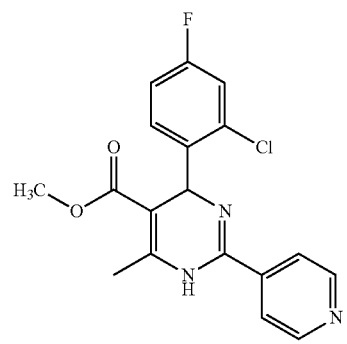

B1

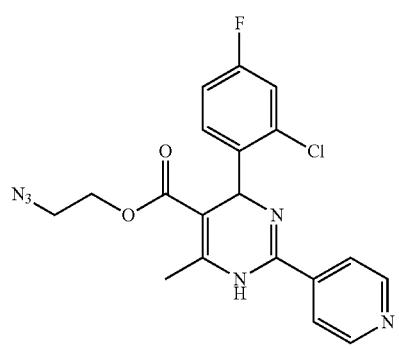

B-2

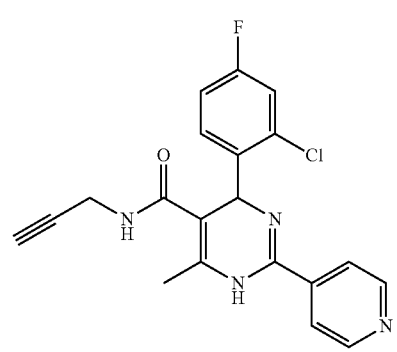

B-3

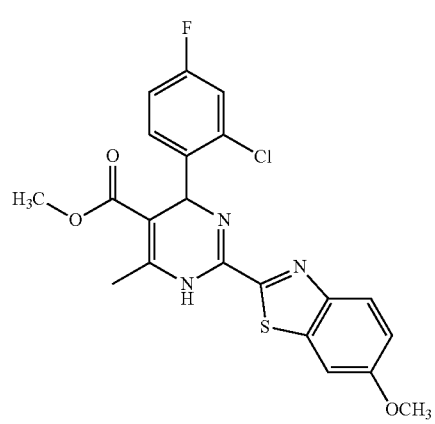

B-4

-continued
B-5
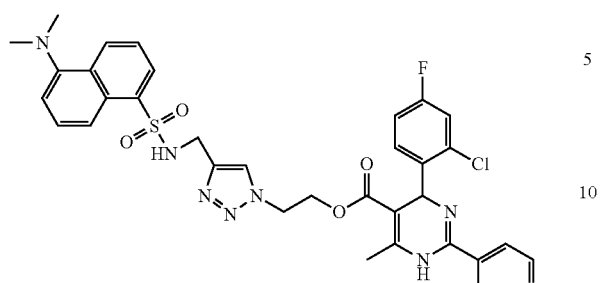
B-7
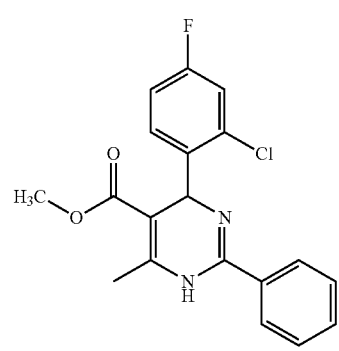
B-8
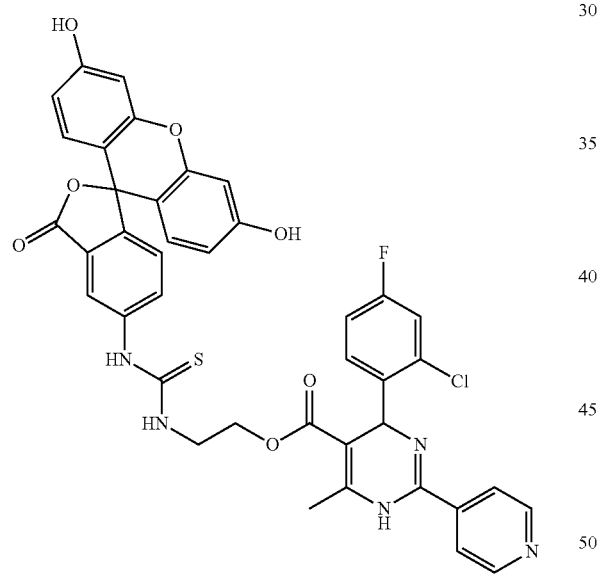
B-11
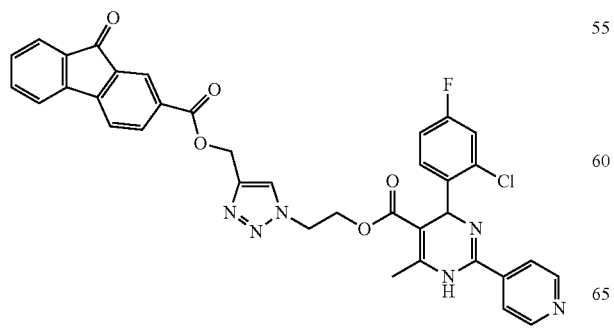
-continued
B-12
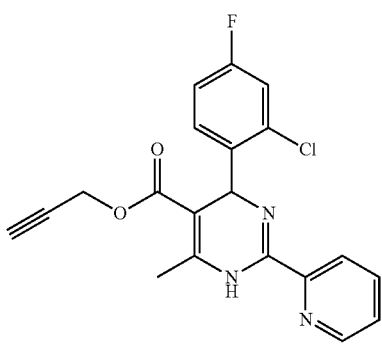
B-13
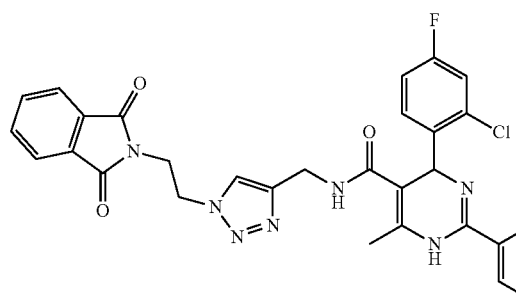
B-15
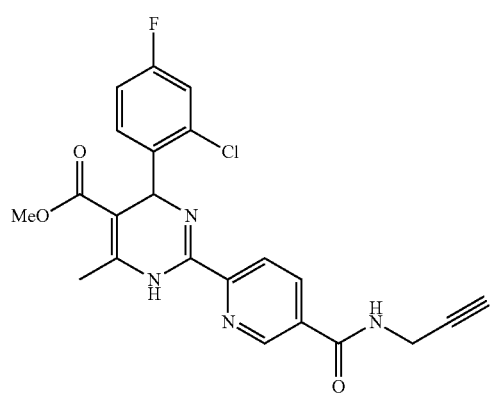
B-17
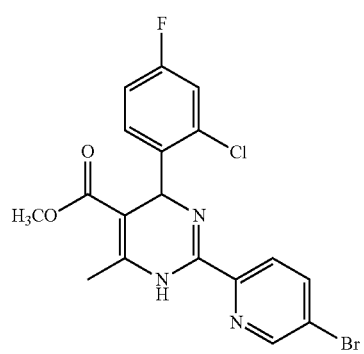

-continued
B-18
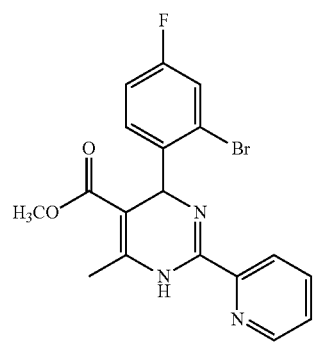
B-23
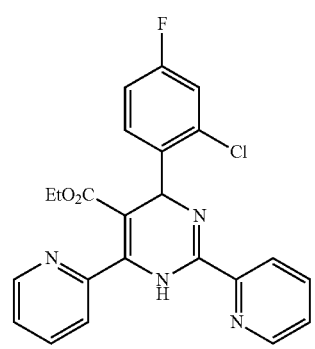
B-51
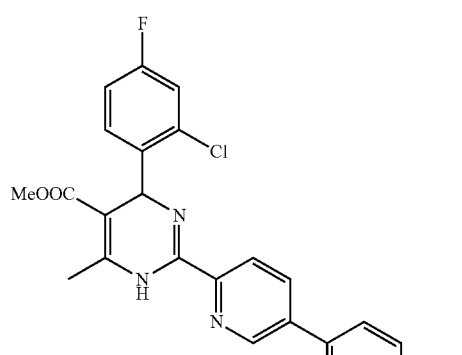
B-67
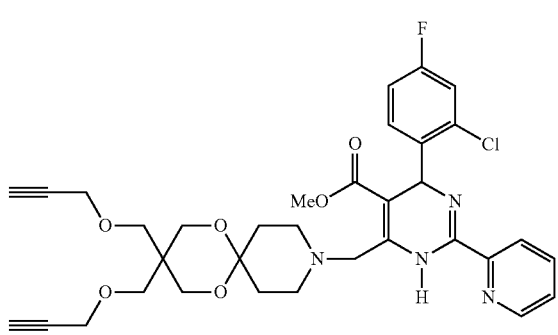
-continued
B-68
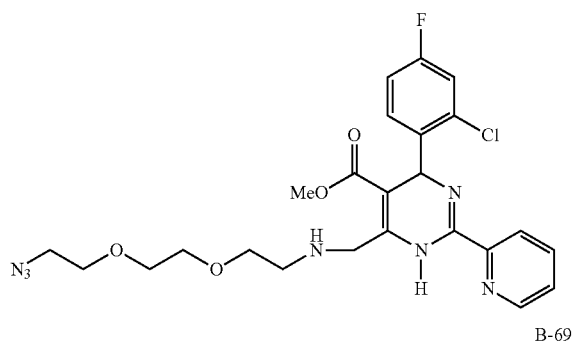
B-69
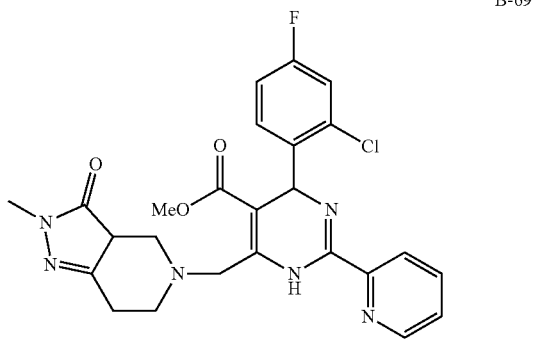
B-70
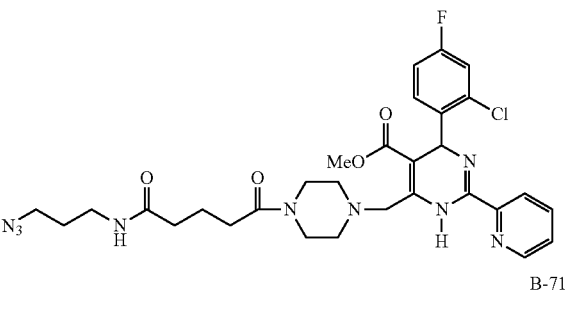
B-71
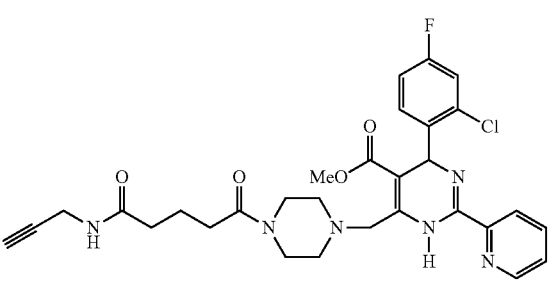
B-72
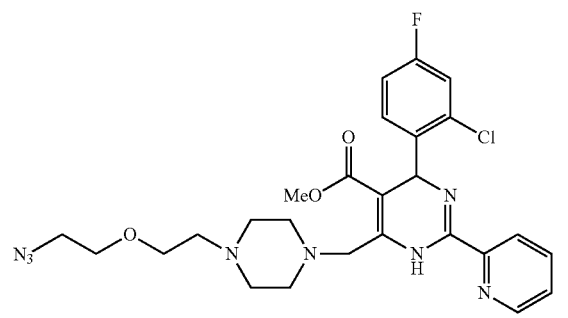

-continued
B-73
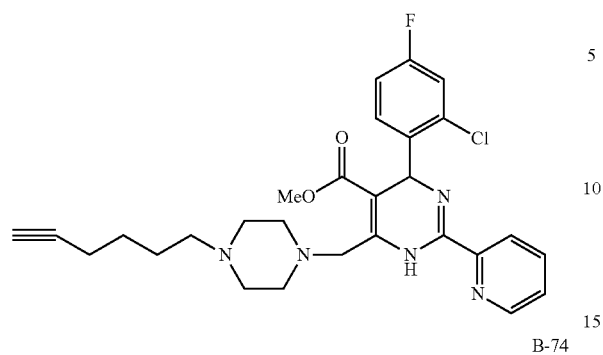
B-74
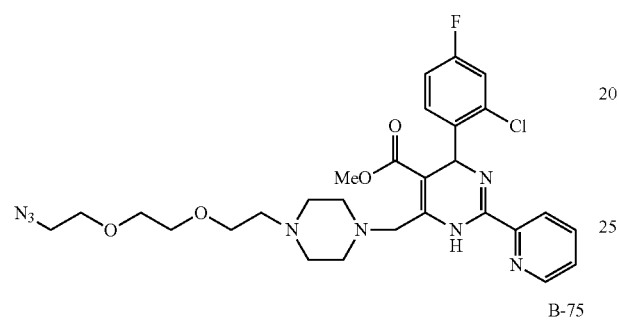
B-75
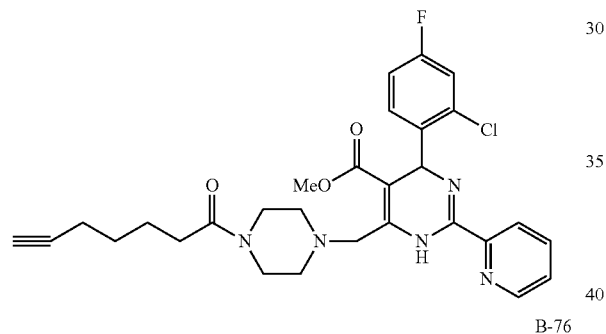
B-76
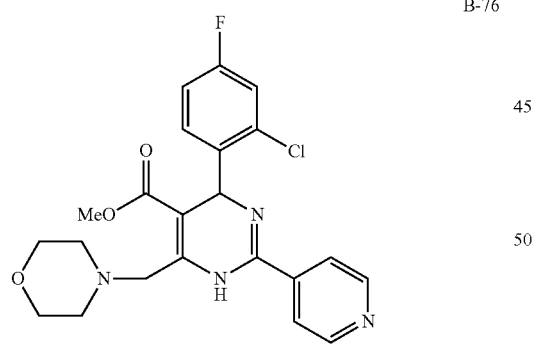
B-77
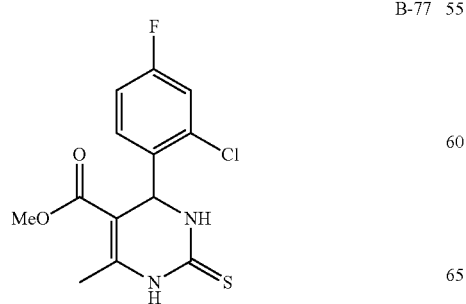
-continued
B-78
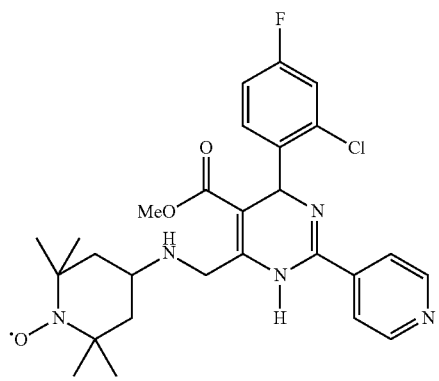
B-79
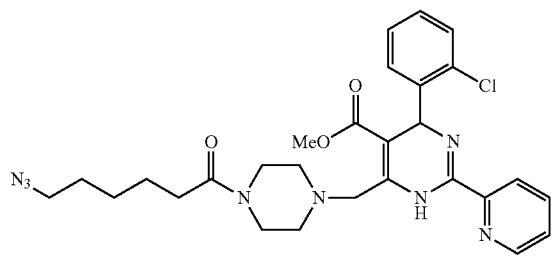
B-80
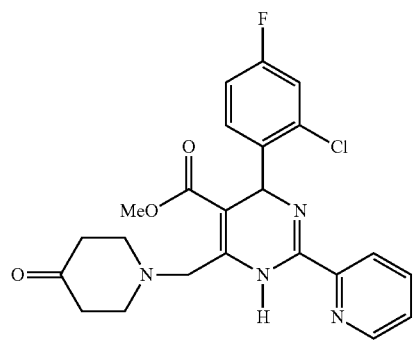
B-81

B-82
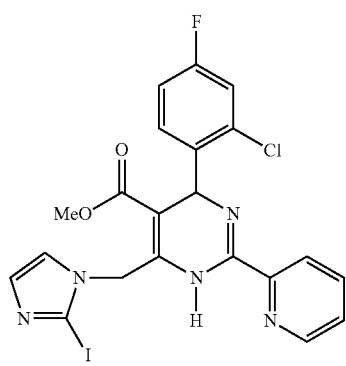
B-83
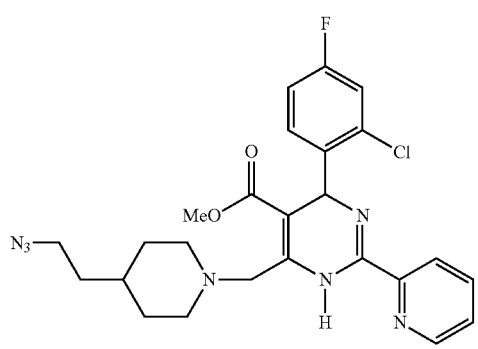
B-84
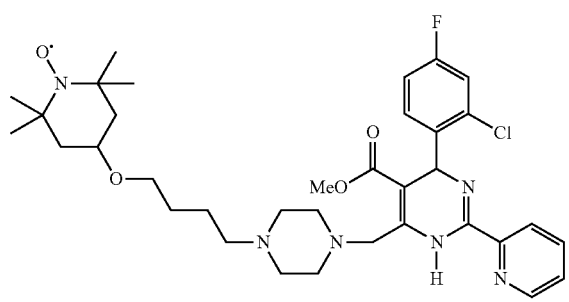
B-101
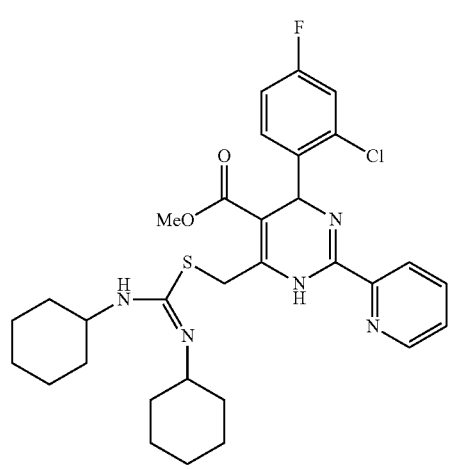
B-102
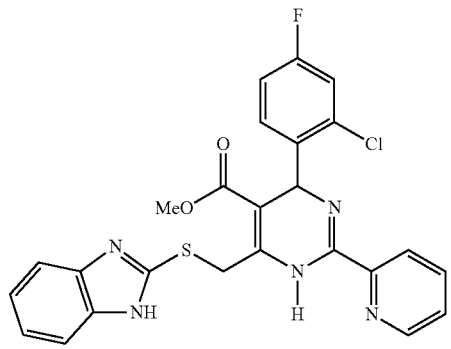
B-103
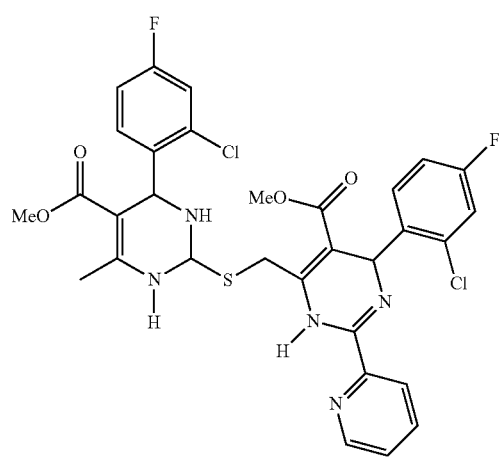
B-104
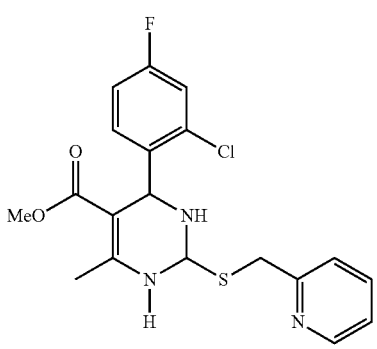
B-105
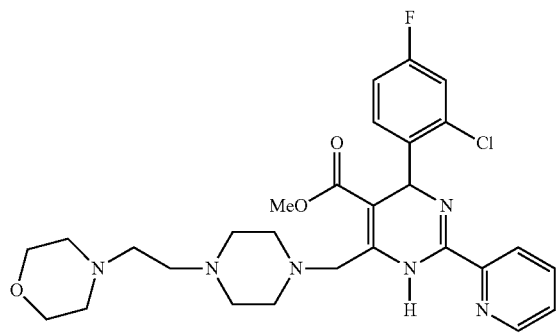

B-106
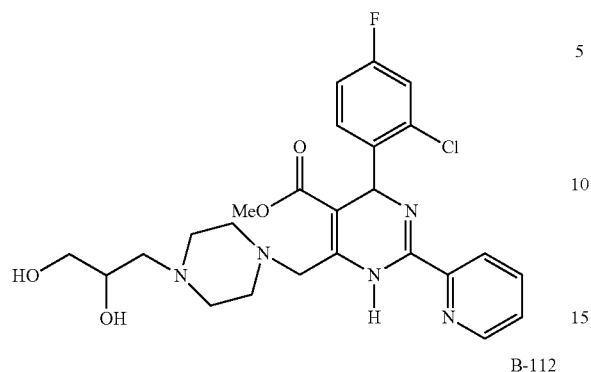
B-112
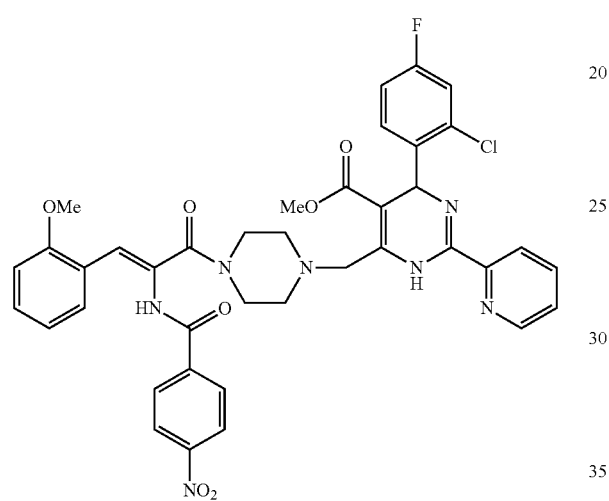
B-104
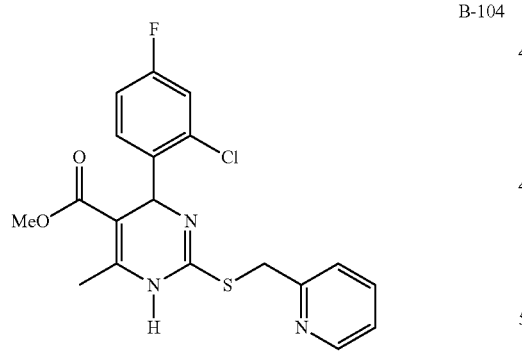
B-114
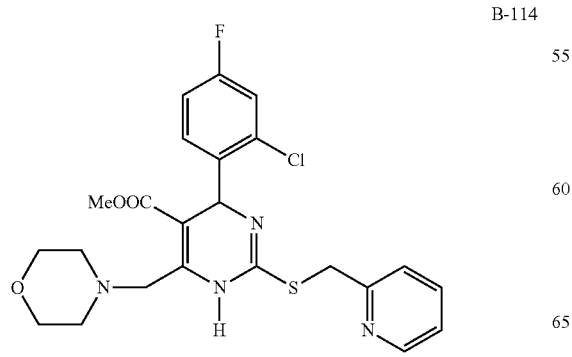
B-115
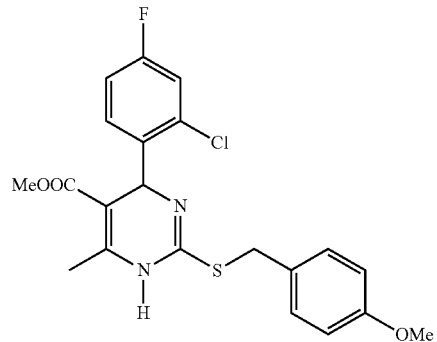
B-116
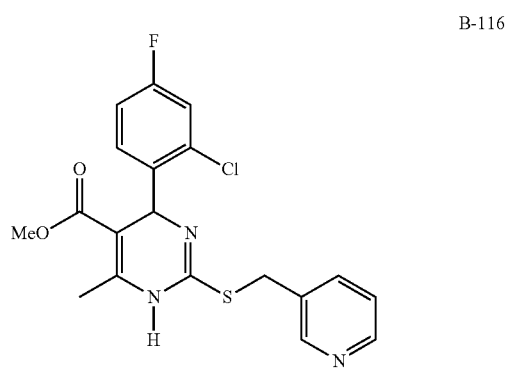
B-117
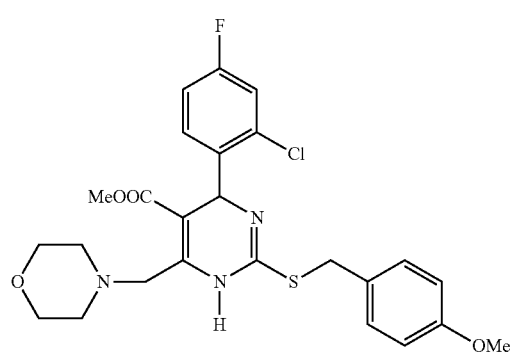
B-120
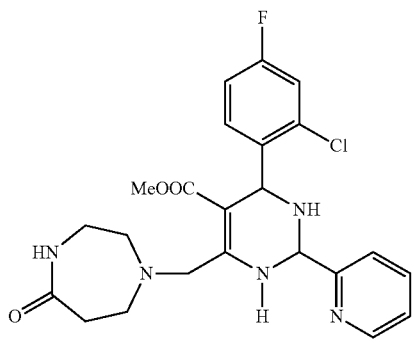

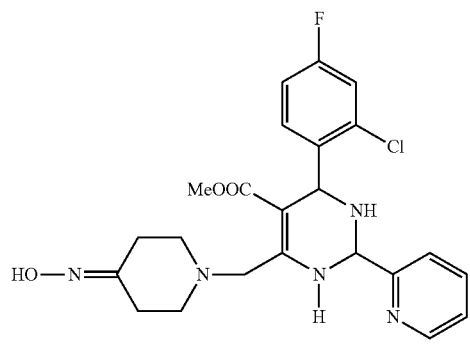
B-121
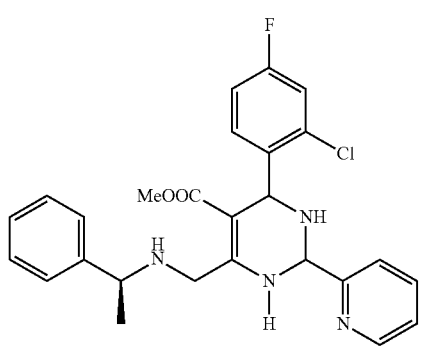
B-122
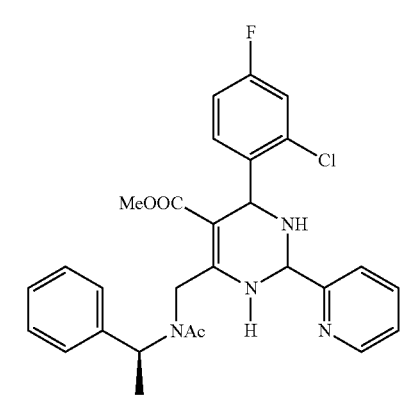
B-123
B-124
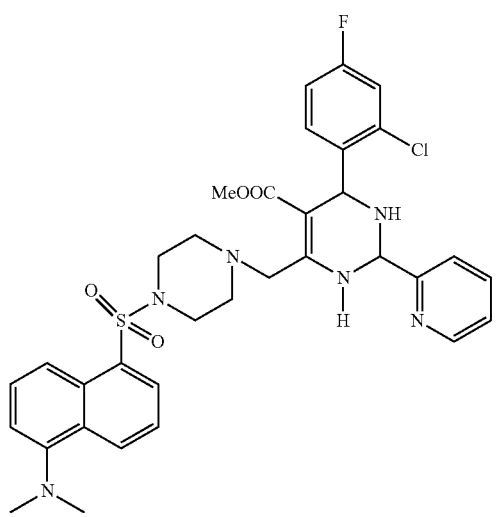
B-125
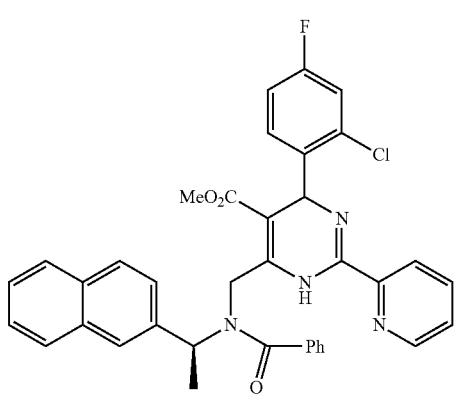
B-126
B-127
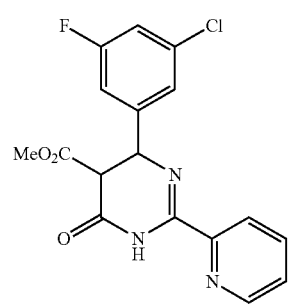
B-130

B-140

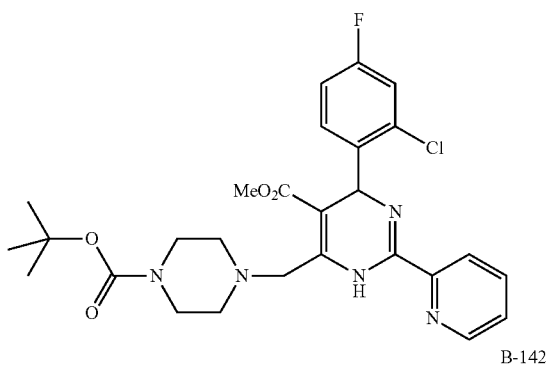

B-142

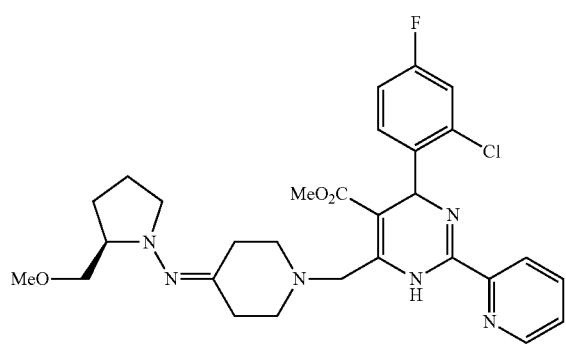

Illustrative derivatives include, but are not limited to, both those compounds that may be synthetically prepared from the compounds described herein, as well as those compounds that may be prepared in a similar way as those described herein, but differing in the selection of starting materials. In addition, it is to be understood that derivatives of those compounds also include the compounds having those same or different functional groups at different positions on the aromatic ring. Similarly, derivatives include parallel variations of other functional groups on the compounds described herein, such as $R^A$, $R^B$, and the like.

It is to be understood that such derivatives may include prodrugs of the compounds described herein, compounds described herein that include one or more protection or protecting groups, including compounds that are used in the preparation of other compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be understood that in certain embodiments, each of the forgoing may be univalent (i.e. attached to the remainder of the formula via one attachment) or multivalent (i.e. attached to the remainder of the formula via more than one attachment). It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_9$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain is cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. It is to be understood that in certain embodiments, each of the forgoing may be univalent (i.e. attached to the remainder of the formula via one attachment) or multivalent (i.e. attached to the remainder of the formula via more than one attachment). Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. It is to be understood that in certain embodiments, each of the forgoing may be univalent (i.e. attached to the remainder of the formula via one attachment) or multivalent (i.e. attached to the remainder of the formula via more than one attachment). In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, aryl alkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, azido, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, azido, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)-Z^x$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1$-$C_6$ alkyl)$(C_1$-$C_6$ alkyl)amino, alkylcarbonylamino, N—$(C_1$-$C_6$ alkyl)alkylcarbonylamino, aminoalkyl, $C_1$-$C_6$ alkylaminoalkyl, $(C_1$-$C_6$ alkyl)$(C_1$-$C_6$ alkyl)aminoalkyl, alkylcarbonylaminoalkyl, N—$(C_1$-$C_6$ alkyl)alkylcarbonylaminoalkyl, cyano, azido, and nitro; or $Z^x$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as $-OH-$, $-SH$, $-CO_2H$, $-NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexyl-carbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3$-$C_{20})$alkanoyl; halo-$(C_3$-$C_{20})$alkanoyl; $(C_3$-$C_{20})$alkenoyl; $(C_4$-$C_7)$cycloalkanoyl; $(C_3$-$C_6)$-cycloalkyl$(C_2$-$C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1$-$C_3)$alkyl and $(C_1$-$C_3)$alkoxy, each of which is optionally further substituted with one or more of 1 to 3 halogen atoms; optionally substituted aryl$(C_2$-$C_{16})$alkanoyl and optionally substituted heteroaryl$(C_2$-$C_{16})$alkanoyl, such as the aryl or heteroaryl radical being unsubstituted or substituted by 1 to 3 substituents selected from the group consisting of halogen, $(C_1$-$C_3)$alkyl and $(C_1$-$C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1$-$C_3)$alkyl, and $(C_1$-$C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

It is to be understood that the embodiments described herein may be combined in all possible chemically relevant ways.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

As used herein, the term "treatment" or "treating" means any administration of a compound or composition described and includes (1) inhibiting the disease in a patient that is experiencing or displaying the pathology or symptomatology of infection by HBV (i.e., arresting further development of the pathology and/or symptomatology), (2) ameliorating the disease in a patient that is experiencing or displaying the pathology or symptomatology of infection by HBV (i.e., reversing or lessening the pathology and/or symptomatology), inhibiting or (4) preventing of chronic infection by HBV. The term "controlling" includes preventing, treating, eradicating, ameliorating or otherwise reducing the severity of the infection by HBV.

The term "administering" as used herein includes all means of introducing the compounds and compositions described herein to the patient, including, but are not limited to, oral (po), intravenous (iv), intramuscular (im), subcutaneous (sc), transdermal, inhalation, and the like. The compounds and compositions described herein may be administered in unit dosage forms and/or formulations containing conventional nontoxic pharmaceutically-acceptable carriers, adjuvants, and vehicles.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions. Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly (lactic acid), poly(glycolic acid) or poly(ortho esters)).

The following examples further illustrate specific embodiments of the invention; however, the following illustrative examples should not be interpreted in any way to limit the invention.

EXAMPLES

Synthesis of a Representative HAP Compound

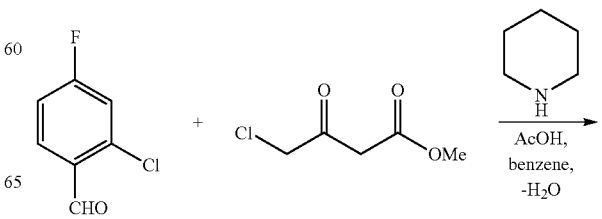

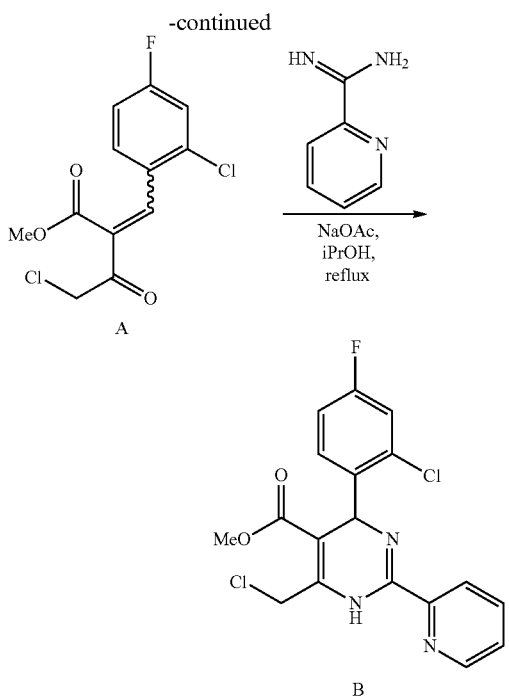

Compound A. A solution of methyl 4-chloroacetoacetate (2.43 mL, 20.0 mmol) and 2-chloro-4-fluorobenzaldehyde (3.3 g, 20.2 mmol) in benzene (30 mL) was placed into a round-bottomed flask equipped with a Dean-Stark trap. Acetic acid (115 µL, 2.0 mmol) and piperidine (200 µL, 2.0 mmol) were added. The mixture was heated at reflux with removal of azeotroped water for 12 h and the resulting mixture was diluted with ether and washed with water and brine. The organic layer was dried over anhydrous $Na_2SO_4$, and the solvent was removed by rotary evaporation. The product was purified by column chromatography (1:10 EtOAc/hexane) to give A (3.8 g, 66%) as a yellow oil. The NMR data showed the material to be composed of a 2:1 mixture of isomers. MS (M+H$^+$, m/z) 291.

Compound B. To a solution of A (3.8 g, 13.2 mmol) in i-PrOH (30 mL) was added 2-amidinopyridinium chloride (2 g, 12.4 mmol) and sodium acetate (123 mg, 1.50 mmol). The mixture was heated at reflux for 12 h, and was then cooled, evaporated, and dissolved in a 1:1 mixture of 0.5 M HCl (aq)/EtOAc (60 mL). The organic layer was extracted with 1 M HCl (20 mL). The combined aqueous layers were washed with ether, rendered basic with ammonia solution (36 wt %), and extracted with EtOAc (3×50 mL). The combined organic layers were washed with water and brine, dried over anhydrous $Na_2SO_4$, and evaporated. The product was purified by column chromatography (1:5 EtOAc/hexane) to give B (2.6 g, 50%) as a yellow solid. MS (M+H$^+$, m/z) 394.

Compound B-120. To a solution of B (30 mg, 0.076 mmol) in DMF (1 mL) was added triethylamine (60 µL, 0.43 mmol) followed by 1,4-diazepan-5-one (45 mg, 0.40 mmol). The mixture was stirring for 24 h at room temperature. The resulting mixture was diluted with EtOAc and washed with brine. The organic layer was dried over $Na_2SO_4$, and evaporation. The product was purified by column chromatography (1:3 EtOAc/hexane) to give 12 (88% yield) as a yellow solid. MS (M+H$^+$, m/z) 472.

Antiviral Activity

Antiviral activity was measured using an inducible HBV expression system, AD38 cells. (Ladner, S. K. et al., *Antimicrob Agents Chemother* 41, 1715-20 (1997)). Initial experiments tested the activity of 10 µM HAP (percentage viral assembly at 24 hour). For active molecules, effective concentrations were determined for suppression of HBV production by 50% and by 90%; this value is reported in µM. Compound toxicity was tested in the parent cell line, HepG2. This is reported as the concentration required to suppress cell growth by 50%, CC50 (in µM) and as the ratio of CC50/EC50, also known as the therapeutic index. As a control and for comparison, the results for the nucleoside analog 3TC (lamivudine) also described. All of these experiments were performed blind, in the laboratory of Raymond Schinazi (Emory University). See TABLE I.

TABLE I

| Compound [ ], at 10 µM | Δ-Ct-HBV | Δ-Ct-HBV-StDev | % Inhibition | HepAD38 EC50, µM | HepAD38 EC90, µM | HepG2 CC50, µM (TI) |
|---|---|---|---|---|---|---|
| B-061 | N/A | N/A | EC$_{50}$ = 0.55 µM | 0.49 | 1 | >100 (>200) |
| B-070 | 9.77 | 0.34 | 99.88 | 2.3 | 5.9 | 8.4 (3.7) |
| B-073 | 1.5 | 0.21 | 64.44 | 7.6 | >10 | 3.7 (0.5) |
| B-078 | −1.01 | 0.39 | <1 | | | |
| B-079 | 10.45 | 0.22 | 99.93 | 1.3 | 2.9 | 61 (47) |
| B-080 | 10.38 | 0.24 | 99.92 | 0.4 | 2.9 | 5.8 (15) |
| B-081 | 10.74 | 0.22 | 99.94 | 4.3 | 8.9 | 4.5 (1.0) |
| B-083 | 1.53 | 0.28 | 65.28 | 7.7 | >10 | 18 (2.3) |
| B-089 | 6.46 | 0.28 | 98.84 | 1.2 | 5.2 | >100 (>83) |
| B-108 | 4.79 | 0.19 | 96.35 | 1.3 | 7.9 | >100 (>77) |
| B-110 | −0.41 | 0.2 | <1 | | | |
| B-120 | 9.65 | 0.57 | 99.87 | 0.3 | 0.9 | 32 (99) |
| B-121 | 9 | 0.27 | 99.8 | 0.4 | 1 | 19 (53) |
| B-122 | 1.52 | 0.28 | 65.06 | 6.9 | >10 | 47 (6.9) |
| B-123 | 0.16 | 0.18 | 10.3 | | | |
| B-124 | 2.87 | 0.25 | 86.2 | 7.6 | >10 | >100 (>11) |
| B-125 | 1.35 | 0.18 | 60.57 | | | |
| B-142 | 7.74 | 0.21 | 99.53 | 5.9 | 9.2 | 5.6 (1.0) |
| 3TC (control) | 6.17 | 0.22 | 98.59 | 0.06 | 0.2 | >100 (>1000) |

Fluorescence Quenching Assay

The table below indicates the extent that different HAPs stimulate assembly of HBV. The assay is based on assembly-dependent fluorescence quenching of the labeled core protein, Cp150Bo. 9 (Stray, S. J., et al., Nat Biotechnol 24, 358-362 (2006); Zlotnick, A., et al., Biochemistry 38, 14644-14652 (1999)). A single time point after assembly is initiated, 24 hr, is presented. The specified HAP was pre-incubated with purified, labeled HBV core protein dimer for at least 20 minutes. Assembly was then initiated by adding NaCl. The conditions were chosen so that Cp150Bo achieve about 30±15% assembly in the absence of stimulation. Because different aberrant complexes may lead to greater quenching than observed in capsid, there are several examples of greater than 100% assembly.

| Compound | Assembly |
|---|---|
| B-6* | 95 |
| B-22 | 77 |
| B-24 | 70 |
| B-25 | 54 |
| B-34 | 65 |
| B-35 | 87 |
| B-36 | 92 |
| B-54 | 21 |
| B-55 | 60 |
| B-56 | 15 |
| B-57 | 49 |
| B-58 | 42 |
| B-59** | 57 |
| B-60** | 60 |
| B-61** | 51 |
| B-1* | 78 |
| B-2 | 51 |
| B-3 | 48 |
| B-4 | 56 |
| B-5 | 54 |
| B-7 | 96 |
| B-8 | — |
| B-12 | 83 |
| B-13 | 55 |
| B-15 | 48 |
| B-16 | 57 |
| B-17 | 87 |
| B-18 | 93 |
| B-19 | 72 |
| B-20 | 75 |
| B-21 | 90 |
| B-26 | 24 |
| B-23 | 47 |
| B67 | 84 |
| B68 | 49 |
| B69 | 54 |
| B70 | 123 |
| B71 | 133 |
| B72 | 29 |
| B73 | 69 |
| B74 | 21 |
| B75 | 134 |
| B76 | 36 |
| B77 | 15 |
| B78 | 75 |
| B79 | 124 |
| B80 | 133 |
| B81 | 129 |
| B82 | 24 |
| B83 | 125 |
| B84 | 63 |
| B101 | 48 |
| B102 | 60 |
| B103 | 60 |
| B104 | 93 |
| B105 | 86 |
| B106 | 59 |
| B112 | 44 |
| B120 | 96 |
| B121 | 97 |
| B122 | 91 |
| B123 | 77 |
| B124 | 94 |
| B125 | 86 |
| B142 | 100 |

-continued

| Compound | Assembly |
|---|---|
| Comparative Examples Follow | |
| B-6* | 95 |
| B-22 | 77 |
| B-24 | 70 |
| B-25 | 54 |
| B-34 | 65 |
| B-35 | 87 |
| B-36 | 92 |
| B-54 | 21 |
| B-55 | 60 |
| B-56 | 15 |
| B-57 | 49 |
| B-58 | 42 |
| B-59** | 57 |
| B-60** | 60 |
| B-61** | 51 |
| B61 | 99 |
| HAP1 | 59 |
| HAP2 | 99 |
| HAP-PI | 60 |
| B-61 | 80 |

Comparative compounds are shown below:

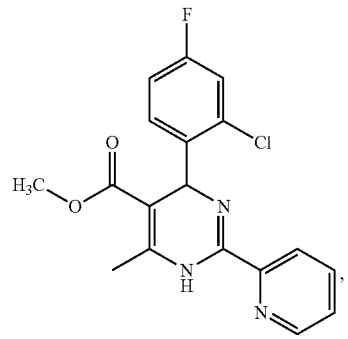

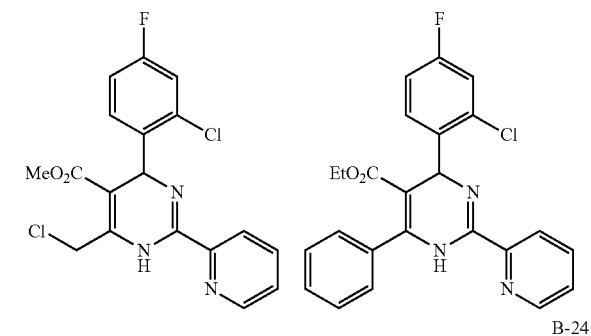

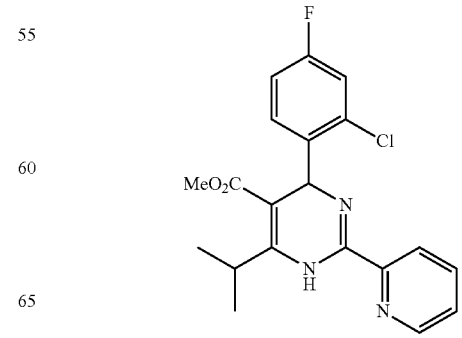

B-25
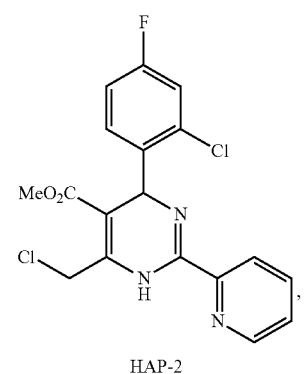
HAP-2
B-48
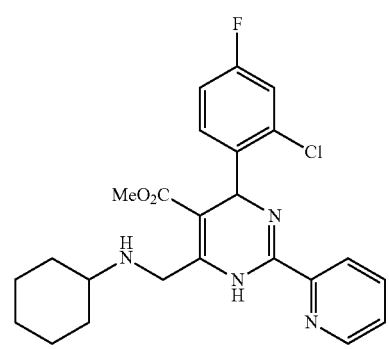
B-49
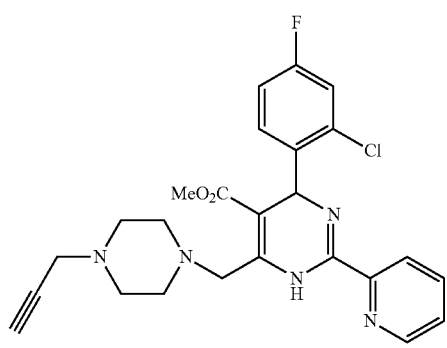
B-50
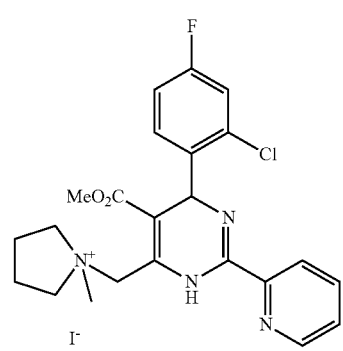
B-34
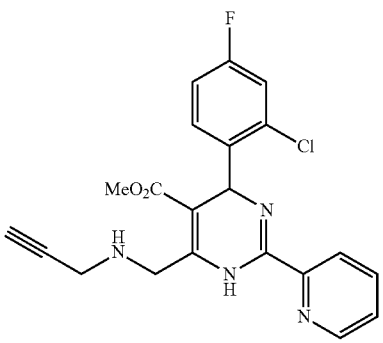
B-35
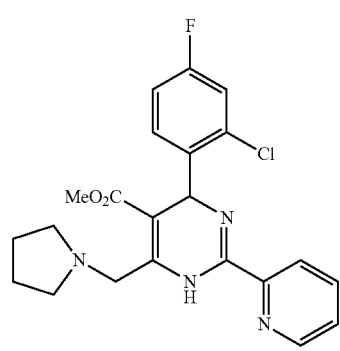
B-36
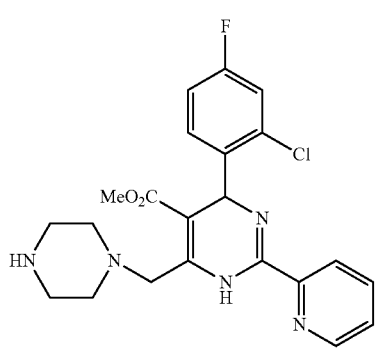
B-52
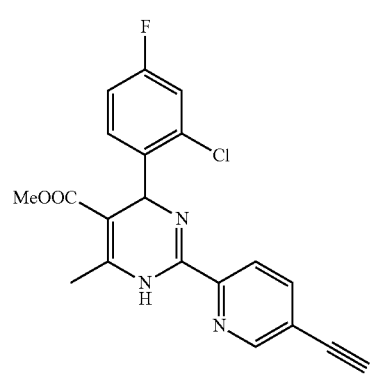

B-54
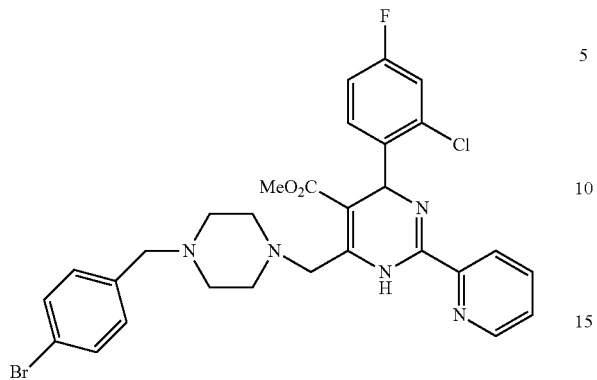
B-55
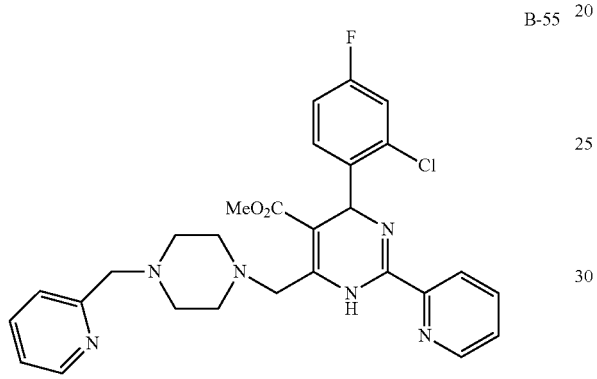
B-56
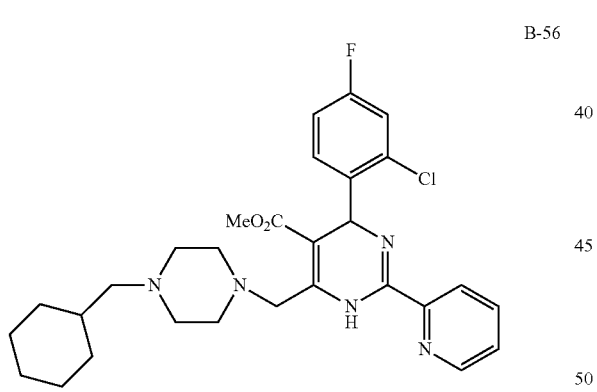
B-57
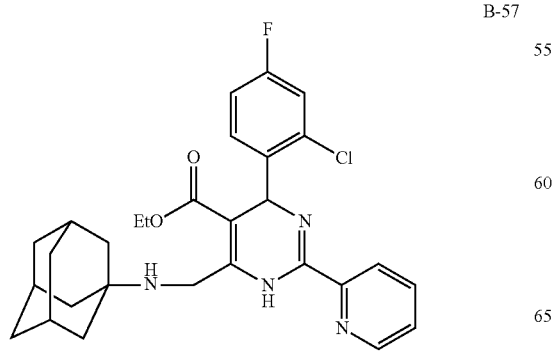
B-58
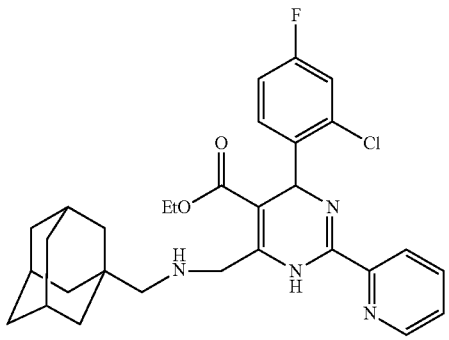
B-59
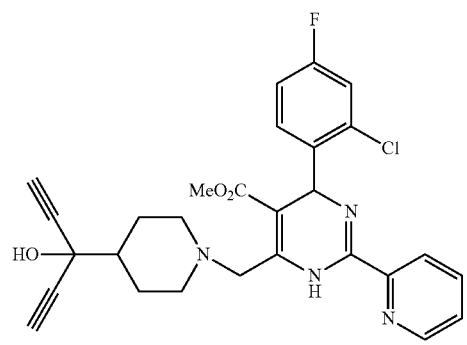
B-60
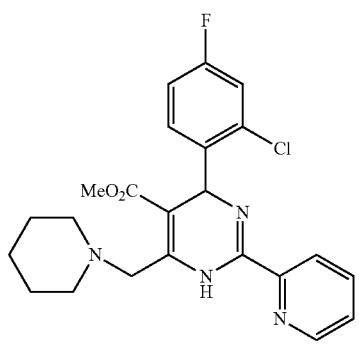
B-61
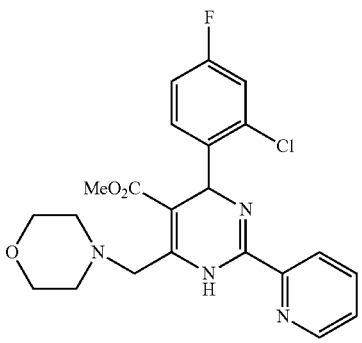

What is claimed is:

1. A compound of the formula

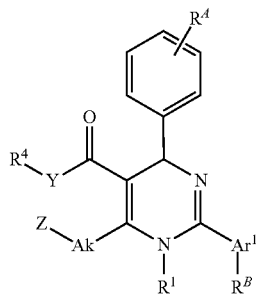

or a pharmaceutically acceptable salt thereof, wherein
Ar¹ is 2-pyridyl;
R¹ is hydrogen;
Ak is methylene;
Z is

where X is —C(O)N(R$^N$)—,
where R$^N$ is selected from the group consisting of H, alkyl, alkenyl, and alkynyl;
R⁴ is alkyl;
Y is O;
R$^A$ represents from 0 to 3 substituents independently selected in each instance from the group consisting of halo, alkyl, and hydroxyl; and
R$^B$ represents from 0 to 3 substituents independently selected in each instance from the group consisting of halo and hydroxyl.

2. The compound of claim 1 wherein R$^A$ represents 2-chloro-4-fluoro.

3. The compound of claim 1 wherein R$^B$ represents 0 substituents.

4. The compound of claim 1 wherein R⁴ is methyl.

5. A pharmaceutical composition comprising a therapeutically effective amount of one or more compounds of claim 1 and an excipient, for treating hepatitis B.

6. A method for treating a patient in need of relief from infection by hepatitis B virus, the method comprising the step of administering to the patient a therapeutically effective amount of one or more compounds of claim 1.

7. The method of claim 6 wherein the treating includes ameliorating symptoms or inhibiting chronic infection by hepatitis B virus.

8. The method of claim 6 wherein the infection is a chronic infection.

9. The method of claim 6 wherein the infection is an acute infection.

10. A compound of claim 1, represented by:

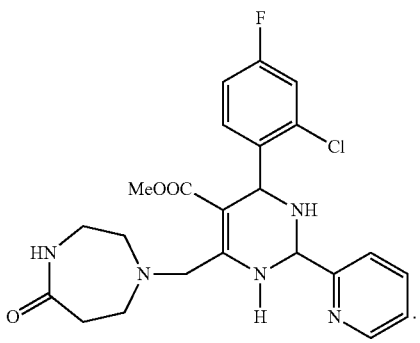 [SMILES: COC(=O)C1=C(CN2CCNC(=O)CC2)NC(c2ccccn2)NC1c1ccc(F)cc1Cl]

11. A compound represented by:

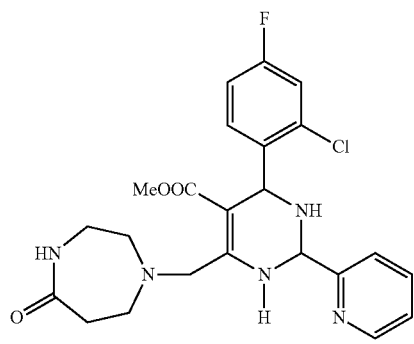 [SMILES: COC(=O)C1=C(CN2CCNC(=O)CC2)NC(c2ccccn2)NC1c1ccc(F)cc1Cl]

or a pharmaceutically acceptable salt thereof.

12. A pharmaceutically acceptable composition comprising a compound of claim 11 and a pharmaceutically acceptable excipient.

* * * * *